United States Patent [19]

Kernstock et al.

[11] Patent Number: 4,552,685

[45] Date of Patent: Nov. 12, 1985

[54] THICKENED AMPHOTERIC SURFACTANT SOLUTIONS

[75] Inventors: John M. Kernstock; Earl H. Johnson; Bertha R. Vaughn, all of Midland, Mich.

[73] Assignee: The Dow Chemical Company, Midland, Mich.

[21] Appl. No.: 124,028

[22] Filed: Feb. 25, 1980

Related U.S. Application Data

[63] Continuation-in-part of Ser. No. 63,280, Aug. 2, 1979, abandoned.

[51] Int. Cl.$^4$ .............................................. B01F 17/00
[52] U.S. Cl. .................................... 252/355; 252/357; 252/356; 252/525; 252/526; 252/527
[58] Field of Search ............... 252/355, 356, 357, 354, 252/525–527, DIG. 13, 544, 545, 546; 424/70

[56] References Cited

U.S. PATENT DOCUMENTS

| | | | |
|---|---|---|---|
| 3,652,497 | 3/1972 | Junas | 260/47 A |
| 3,708,445 | 1/1973 | Junas | 260/40 R |
| 3,712,918 | 1/1973 | Dudzinski et al. | 260/527 |
| 3,894,980 | 7/1975 | Tommaso | 252/355 |
| 3,996,146 | 12/1976 | Farasov | 424/70 |
| 4,126,674 | 11/1978 | Mausner | 252/DIG. 3 |
| 4,221,733 | 9/1980 | Melloh et al. | 424/70 |
| 4,233,192 | 11/1980 | Lindemann | 424/70 |
| 4,243,659 | 1/1981 | Balingit et al. | 424/70 |

*Primary Examiner*—A. Lionel Clingman
*Attorney, Agent, or Firm*—P. D. Shepherd; A. J. Borschke

[57] ABSTRACT

Aqueous compositions containing a water-soluble amphoteric surfactant are effectively thickened without substantial loss in clarity by a suitable pH responsive, synthetic addition copolymeric thickener such as a copolymer of an $\alpha,\beta$-ethylenically unsaturated carboxylic acid (e.g., methacrylic acid), a nonionic chain extender of an $\alpha,\beta$-ethylenically unsaturated monomer (e.g., ethyl acrylate), and a nonionic vinyl surfactant ester (e.g., nonylphenoxy(polyethyleneoxy)ethyl methacrylate). Due to the ability of the copolymeric thickener to increase the viscosity of the amphoteric surfactant composition without substantially reducing the clarity thereof, the resulting thickened compositions are useful as shampoos, cleaning compounds and the like.

18 Claims, No Drawings

THICKENED AMPHOTERIC SURFACTANT SOLUTIONS

CROSS-REFERENCE TO RELATED APPLICATION

This application is a continuation-in-part of our copending application Ser. No. 063,280, filed Aug. 2, 1979 now abandoned.

BACKGROUND OF THE INVENTION

The present invention relates to thickened aqueous compositions containing an amphoteric surfactant, particularly to those compositions thickened with a synthetic, addition copolymer.

Cosmetic cleansers such as shampoos, soaps and the like consist of various ingredients including surfactants, preservatives and foam stabilizers, each of which performs a different specialized function, e.g., cleaning, foam boosting and the like. Often a harsh anionic or cationic surfactant, e.g., sodium lauryl sulfate or a quaternary fatty amine, is employed in such cleanser compositions to impart the required cleansing properties thereto.

Inasmuch as shampoo compositions containing such anionic or cationic surfactants are generally not sufficiently viscous for many applications, it has become a common practice to add a thickener thereto. Conventional thickeners employed heretofore include the cellulose ethers, e.g., methyl cellulose; certain synthetic addition copolymers such as polyvinyl acetate maleate or a copolymer of maleic anhydride, an alkyl vinyl ether and a hydrocarbon oxyalkylene vinyl ether; and combinations of a cellulose ether and a synthetic addition copolymer. See, for example, U.S. Pat. Nos. 2,645,615; 3,499,876 and 3,485,915. Alternatively, surfactant combinations such as the combination of sodium lauryl sulfate and a sulfonated amine, e.g., Sandopan TFL Conc. ®, are known to provide a thickened shampoo composition. See, for example, *Journal of the American Oil Chemists' Society*, Volume 49, June, 1972, Peter M. Hay, "Synergistic Interactions of Shampoo Ingredients", pages 343–345.

Unfortunately, to provide the desired cleansing properties, the shampoo often contains an amount of the cationic or anionic surfactant sufficient to render the shampoo composition relatively alkaline (e.g., pH of above about 9) or acidic (e.g., pH of below about 5) and to cause significant eye irritation. To alleviate the problems associated with the harsh cationic or anionic surfactant, amphoteric surfactants are employed in many shampoo formulations, particularly the so-called baby shampoos. The amphoteric surfactants have been found to provide suitable cleansing activity while greatly reducing eye irritation. Unfortunately, many of the conventional thickeners do not effectively thicken the shampoo compositions or other aqueous solutions containing amphoteric surfactants.

In view of the aforementioned deficiencies associated with thickening aqueous solutions of amphoteric surfactants, it remains highly desirable to furnish an aqueous composition of an amphoteric surfactant which is effectively thickened.

SUMMARY OF THE INVENTION

Accordingly, the present invention is a thickened aqueous composition of an amphoteric surfactant which comprises an aqueous solution of a watersoluble amphoteric surfactant thickened with a pH responsive, synthetic addition polymer which is insoluble in an aqueous liquid at a pH of less than about 2, said composition being at a pH and containing an amount of the pH responsive copolymer sufficient to increase the viscosity of the amphoteric surfactant composition without substantially reducing the clarity thereof.

Another aspect of this invention is a method for preparing a thickened, amphoteric surfactant composition, said method comprising the step of thickening an aqueous solution of a water-soluble amphoteric surfactant with an amount of the pH responsive, synthetic addition copolymer sufficient to increase the viscosity of the amphoteric surfactant solution without substantially reducing the clarity thereof.

Surprisingly, the thickened amphoteric surfactant compositions of the present invention exhibit significantly higher viscosities than identical amphoteric surfactant compositions which do not contain the copolymeric thickener, without a substantial loss in clarity. Moreover, the foaming properties and surface tension of the thickened amphoteric surfactant composition are not substantially reduced.

For these reasons, the thickened amphoteric surfactant compositions of this invention are useful as cosmetic cleaners such as hair shampoos and conditioners, hand cleaners and liquid soaps; rug shampoos; industrial cleaners; release coatings and the like.

In a preferred embodiment of this invention, the copolymeric thickener is a copolymer (hereinafter referred to as a surfactant ester copolymer) of an $\alpha,\beta$-ethylenically unsaturated carboxylic acid; a non-ionic $\alpha,\beta$-ethylenically unsaturated surfactant ester; and a polymeric chain extender of a nonionic $\alpha,\beta$-ethylenically unsaturated monomer (hereinafter referred to as nonionic chain extender) which is copolymerizable therewith. In said embodiment, the $\alpha,\beta$-ethylenically unsaturated carboxylic acids are preferably of the formula:

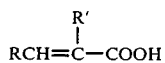

wherein R is —H, —COOX or —CH$_3$; R' is —H, an alkyl group or —CH$_2$COOX and X is —H or an alkyl group; the unsaturated surfactant esters are preferably of the formula:

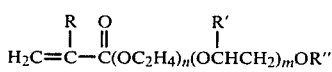

where R is —H or —CH$_3$; R' is an alkyl group or an alkylphenyl group; each R' is individually —H, —CH$_3$ or —C$_2$H$_5$, n is an integer from about 0 to 100 and m is an integer from about 0 to about 100, wherein the sum of n+m is at least about 1 and n is advantageously 1 or more and greater than m; and the nonionic chain extender is preferably represented by the formula:

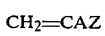

wherein A is —H, —CH$_3$ or a halogen and Z is —COOX where X is an alkyl group or a hydroxyalkyl group; —C$_6$H$_4$Y' where Y' is —H, an alkyl group or a halogen; —CN; —Cl; —Br;

where Z' is an alkyl group; or —CH=CH$_2$.

The surfactant ester copolymers are the preferred copolymeric thickeners due to their ability to impart the most desirable balance of viscosity and clarity properties to the amphoteric surfactant composition without significantly reducing the mildness thereof. In addition, these copolymers are generally more efficient thickeners, i.e., lesser amounts of the copolymer are required to impart the desired thickening to the amphoteric surfactant composition.

DETAILED DESCRIPTION OF THE PREFERRED EMBODIMENTS

For the purposes of this invention, a water-soluble amphoteric surfactant is an amphoteric surfactant which forms at least about a 0.5, preferably at least about a 2, weight percent solution when dispersed in an aqueous liquid. By the term "soluble" it is meant that the surfactant forms a true solution with the aqueous liquid, i.e., individual molecules of the surfactant are uniformly dispersed in the water.

In this invention, the term "surfactant" is used conventionally and generally refers to any surface active agent including those materials conventionally called detergents, emulsifiers and wetting agents which reduce surface tension when dissolved in water or an aqueous liquid or which reduces interfacial tension between two liquids or a liquid and a solid. By the term "amphoteric (or zwitterionic) surfactant" is meant a surfactant having the capacity to act as either an acid or a base, i.e., functioning as a cationic material in an acid medium and as an anionic material in an alkaline medium.

Illustrative examples of amphoteric surfactants are presented in *McCutcheon's Detergents and Emulsifiers*, edited by J. W. McCutcheon, published in 1976 by John W. McCutcheon, Inc., Morristown, N.J. and *CTFA Cosmetic Ingredient Dictionary*, edited by N. F. Estrin, published in 1977 by Cosmetic Toiletry and Fragrance Association, Inc., Washington, D.C., pp. 24–27. Representative of such disclosed amphoteric surfactants advantageously employed herein are the alkyl-substituted imidazolines including monocarboxylated imidazolines (e.g., 2-alkyl-1-carboxymethyl-1-hydroxyethyl-2-imidazoline), dicarboxylated imidazolines (e.g., 2-alkyl-1-carboxymethyl-1-carboxy methyl hydroxyethyl imidazoline) and carboxylated/sulfated imidazoline (e.g., 2-alkyl-1-carboxymethyl hydroxyethyl-1-alkyl sulfate imidazoline) wherein the alkyl groups are derived from an acid such as coconut, lauric, capric, caprylic, ethyl hexoic, oleic, linoleic or stearic acid, the alkyl aminobetaines wherein the alkyl is a group such as coco, decyl, tallow, stearyl, lauryl or cetyl; N-alkyl β-aminopropionic acids and alkyl-3-aminopropionic acids or alkali metal salts thereof wherein the alkyl is a group such as coco, tallow, lauryl, stearyl or myristyl; fatty acid amide sulfonates wherein the fatty acid is an acid such as stearic, lauric, capric, oleic, caprylic or linoleic; and the like. Preferred amphoteric surfactants employed herein are the alkyl substituted imidazolines, particularly the mono- and dicarboxylated imidazolines and the alkyl aminobetaines, particularly decyl betaine, coco betaine, lauryl betaine and cetyl betaine.

The amount of the amphoteric surfactant in the thickened, amphoteric surfactant compositions of this invention can range from a measurable amount to over 99 weight percent based on the weight of the surfactant and the aqueous liquid. In the normal practice of this invention, the thickend amphoteric surfactant composition will advantageously consist of from about 1 to about 35, preferably from about 2 to about 20, more preferably from about 5 to about 15, weight percent of the water-soluble amphoteric surfactant, said weight percent being based on the total weight of amphoteric surfactant and aqueous liquid.

Copolymers suitably employed as the copolymeric thickeners in this invention are pH responsive, synthetic addition copolymers (hereinafter referred to as "copolymeric thickeners") which are capable of thickening an aqueous, amphoteric surfactant solution without substantially reducing the clarity thereof. Advantageously, such copolymers do not deleteriously affect the other properties of the surfactant solution, e.g., does not significantly affect mildness or wetting, when employed in the practice of this invention.

By the term "pH responsive" is meant that the properties and characteristics of the copolymeric thickeners vary with pH wherein the copolymer is generally insoluble in an aqueous liquid having a pH of less than about 2 but dissolves or swells in a neutral or alkaline aqueous liquid. The ability of the copolymer to thicken is primarily due to this conversion of a copolymer which is insoluble (hydrophobic) in an aqueous liquid at one pH, thereby causing no or little viscosity increase in the aqueous liquid, to a copolymer which dissolves or sufficiently swells (hydrophilic) in an aqueous liquid at a second pH to increase the viscosity, i.e., thicken the liquid. Advantageously, the copolymeric thickeners are essentially completely insoluble (form no more than about a 0.5, preferably no more than about a 0.2, more preferably no more than about a 0.1, weight percent solution) in an aqueous liquid having a pH of less than about 3, preferably less than about 4, more preferably less than about 4.5. Alternatively, as the pH of the aqueous liquid is raised to make the liquid neutral or alkaline, the copolymer dissolves or swells extensively in the liquid. Preferably, the copolymer is readily dissolved or sufficiently swollen in an aqueous liquid having a pH of about 6.5, more preferably a pH of about 5.5, to cause thickening.

The compositions of this invention contain an amount of the pH responsive copolymer at a pH such that the copolymer dissolves or swells sufficiently to increase the viscosity of the amphoteric surfactant solution without substantially reducing the viscosity thereof. By "increase the viscosity of the amphoteric surfactant solution" is meant that the viscosity of the aqueous solution of the amphoteric surfactant thickened with the copolymeric thickener, i.e., the thickened amphoteric surfactant composition, is measurably higher than the amphoteric surfactant solution containing no thickener. For the purposes of this invention, viscosity is measured using conventional techniques such as using a Brookfield viscometer, Model LVT, using Spindle Nos. 3 and 4 at 12 rpm and 25° C. Preferably, the viscosity of the aqueous solution of the amphoteric surfactant thickened with a copolymeric thickener of this invention is at least 500, more preferably at least about 1000, most preferably at least about 1500, percent higher than the viscosity of the solution having no thickener therein.

The clarity of the amphoteric surfactant solution is not substantially reduced when the clarity of the solution thickened with the copolymeric thickener, i.e., the thickened, amphoteric surfactant composition, appears clear to the naked eye, i.e., has a light transmittance of at least 50 percent when measured by a UV spectrophotometer such as a Beckman UV spectrometer, Model DB-G. Advantageously, the clarity of the thickened amphoteric surfactant composition is essentially equivalent to an identical amphoteric surfactant composition having no copolymeric thickener therein. By "essentially equivalent" it is meant that the light transmittance of the thickened composition is at least about 80 percent of the light transmittance of the unthickened solution. Preferably, the light transmittance of the thickened composition is at least 90 percent of the unthickened solution.

In general, suitable copolymeric thickeners are anionic copolymers of an $\alpha,\beta$-ethylenically unsaturated carboxylic acid (including maleic anhydride) and one or more other ethylenically unsaturated monomers copolymerizable therewith. A representative example of such a copolymeric thickener is a copolymer of (a) an $\alpha,\beta$-ethylenically unsaturated carboxylic acid, preferably methacrylic acid, and (b) an alkyl ester of an $\alpha,\beta$-ethylenically unsaturated carboxylic acid such as ethyl acrylate or methyl methacrylate, preferably those copolymers wherein the unsaturated carboxylic acid constitutes from about 8 to about 70 weight percent and the ester constitutes from about 92 to about 30 weight percent based on the total weight of the alkyl ester and the acid. Similarly, a copolymer of (a) a vinyl ester of a nonaddition polymerizable carboxylic acid (advantageously, a vinyl ester of an aromatic and saturated aliphatic, i.e., alkanoic, carboxylic acid having from about 2 to about 10 carbon atoms) such as vinyl acetate, vinyl propionate and vinyl benzoate; (b) a nitrile, a hydroxyalkyl ester (advantageously wherein the hydroxyalkyl group contains from about 2 to about 4 carbon atoms) or an alkyl ester of an $\alpha,\beta$-ethylenically unsaturated carboxylic acid (advantageously, wherein the alkyl ester group contains from about 1 to about 8 carbon atoms) (e.g., acrylonitrile, 2-hydroxyethyl acrylate or ethyl acrylate); and (c) an $\alpha,\beta$-ethylenically unsaturated carboxylic acid such as methacrylic acid can be employed herein. Advantageously, such copolymer comprises, in polymerized form, from about 40 to about 90 weight percent of the vinyl ester; from about 5 to about 55 weight percent of the nitrile or the alkyl ester or hydroxyalkyl ester of an unsaturated carboxylic acid; and from about 5 to about 15 weight percent of the unsaturated carboxylic acid.

The preferred copolymeric thickener is a surfactant ester copolymer derived from (a) an $\alpha,\beta$-ethylenically unsaturated carboxylic acid, (b) a nonionic surfactant ester of a polyoxyalkylene derivative of an $\alpha,\beta$-ethylenically unsaturated carboxylic acid and (c) a copolymer chain extender of an $\alpha,\beta$-ethylenically unsaturated monomer copolymerizable with the unsaturated carboxylic acid and the unsaturated surfactant ester.

Of the monomers employed in the preparation of the preferred surfactant ester copolymer, the $\alpha,\beta$-ethylenically unsaturated carboxylic acids advantageously contain from about 3 to about 8 carbon atoms and are preferably of the formula:

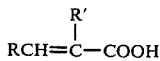
                     I wherein R is —H, —COOX or —CH$_3$ and R' is —H, an alkyl group, preferably having from about 1 to about 4 carbon atoms, or —CH$_2$COOX; wherein X is —H or an alkyl group, preferably having from about 1 to about 4 carbon atoms. Preferably, if R is —COOX, R' is —H or —CH$_2$COOX and if R is CH$_3$, then R' is H. Most preferably, the unsaturated acid is acrylic or methacrylic acid or a mixture of acrylic or methacrylic acid with itaconic or fumaric acid. Less preferably, crotonic and aconitic acid and half esters of these and other polycarboxylic acids such as maleic acid with C$_1$-C$_4$ alkanols are advantageously employed herein, particularly if used in combination with minor amounts of acrylic or methacrylic acid.

The nonionic surfactant esters of polyoxyalkylene derivatives of an $\alpha,\beta$-ethylenically unsaturated carboxylic acids advantageously are preferably represented by the formula:

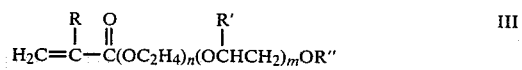
                     III where R is —H or —CH$_3$; R' is —H or an alkyl group, advantageously having 1 or 2 carbon atoms, R" is an alkyl group, advantageously having from about 1 to about 20 carbon atoms, or an alkylphenyl group, advantageously having from about 8 to about 16 carbon atoms, n and m are each integers between about 0 and about 100, wherein the sum of n+m is at least 1, advantageously from 1 to about 100, preferably from about 6 to about 20 and n is preferably 1 or more and greater than m.

The unsaturated surfactant ester significantly affects the properties of the copolymeric thickeners prepared therefrom and the especially preferred unsaturated surfactant esters are selected on the basis of the desired properties of the copolymeric thickener. For example, the hydrophilic-lipophilic balance (HLB) of the surfactant ester monomer has been found to affect the performance of the resulting surfactant ester copolymer. For example, increasing the chain length of the terminal alkyl or alkylphenyl group generally increases the efficiency of the polymer to thicken. In addition, decreasing the number of polyethyleneoxy groups has been generally found to increase thickening efficiency.

In general, the especially preferred unsaturated surfactant esters are the acrylate and methacrylate surfactant esters, with the alkylphenoxypoly(ethyleneoxy)ethyl acrylates of the formula:

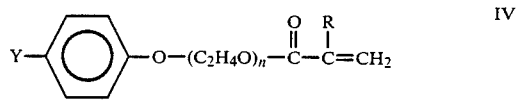
                     IV wherein R is —H or —CH$_3$, Y is an alkyl group, preferably having from about 8 to about 16 carbon atoms and n is from 2 to about 100; the alkoxypoly(ethyleneoxy)ethyl acrylates of the formula:

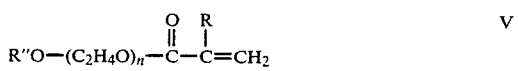
                     V wherein R is —H or —CH$_3$, R" is an alkyl group, advantageously having from about 8 to about 20 carbon atoms and n is between about 6 and about 50; and the alkoxypoly(alkyleneoxy)ethyl acrylates of the formula:

$$R''O-(CH_2CHO)_n(C_2H_4O)_m-C_2H_4O-\overset{O}{\overset{\|}{C}}-\overset{R}{\overset{|}{C}}=CH_2 \qquad VI$$
$$\phantom{R''O-(CH_2}\overset{|}{\underset{R'}{}}$$

wherein R is —H or —CH$_3$, R' is —CH$_3$ or —C$_2$H$_5$, R" is an alkyl group, advantageously having from about 1 to about 20 carbon atoms, n is between about 6 and about 50, and m is between about 1 and about 40.

Such unsaturated surfactant esters are prepared using conventional techniques known in the art. Illustrative of such techniques are U.S. Pat. Nos. 4,075,411 and 2,786,080, which are hereby incorporated by reference. In general, the unsaturated surfactant esters are prepared by the acid catalyzed condensation reaction of a nonionic polyoxyalkylene surfactant alcohol such as alkylphenoxypoly(ethyleneoxy)ethyl alcohol with an excess amount of the desired α,β-ethylenically unsaturated carboxylic acid. Typically, strong acids such as sulfuric acid, preferably as an aqueous solution of at least about 90 weight percent acid; p-toluenesulfonic acid; or a strong acid cation exchange such as DOWEX ® 50 are advantageously employed as the acid catalyst. In general, the moles of the unsaturated carboxylic acids are advantageously employed at from about 4 to about 25 times the moles of the surfactant alcohol employed. Reaction temperature of from about 100° to about 120°C. generally give about 70 to about 90 percent conversion in periods from about 2 to about 4 hours.

The nonionic chain extender is a nonionic α,β-ethylenically unsaturated monomer which is copolymerizable with the unsaturated carboxylic acid and unsaturated surfactant ester and is employed to extend the chain of the surfactant ester copolymer molecule. Preferably, the nonionic chain extender is of the formula:

$$CH_2=CAZ \qquad II$$

where A is —H, —CH$_3$ or a halogen and Z is —COOX' wherein X' is an alkyl group, advantageously containing from about 1 to about 8 carbon atoms, or a hydroxyalkyl group, advantageously containing from about 2 to about 8 carbon atoms; —C$_6$H$_4$Y' wherein Y' is H, an alkyl group, advantageously having from about 1 to about 4 carbon atoms; —CN; Br; Cl;

$$-O\overset{O}{\overset{\|}{C}}Z' \qquad VII$$

wherein Z' is an alkyl group, advantageously having from about 1 to about 8 carbon atoms and —CH=CH$_2$. Of such monomers, those advantageously employed in the practice of this invention include the alkyl esters of methacrylic or acrylic acid, preferably wherein the alkyl group has from about 1 to about 8 carbon atoms such as ethyl acrylate, ethyl methacrylate, methyl methacrylate, 2-ethylhexyl acrylate, butyl acrylate and butyl methacrylate; the hydroxyalkyl esters of acrylic and methacrylic acid, wherein the hydroxyalkyl group contains from about 2 to about 8 carbon atoms such as 2-hydroxyethyl acrylate and 2-hydroxybutyl acrylate; styrene; vinyltoluene; t-butylstyrene; isopropylstyrene; p-chlorostyrene; vinyl acetate; vinyl butyrate; vinyl caprolate; acrylonitrile; methacrylonitrile; butadiene; isoprene; vinyl chloride; vinylidene chloride; and the like. In the practice of this invention, a monovinyl ester such as ethyl acrylate or a mixture thereof with styrene, hydroxyethyl acrylate, acrylonitrile, vinyl chloride or vinyl acetate is most preferably employed.

The properties of the described surfactant ester copolymer, e.g., its ability to thicken, will vary with the type and proportion of each of the monomeric components employed. In general, the monomers and their proportions are advantageously selected on the basis of the desired polymeric properties. Generally, the surfactant ester copolymer is advantageously composed, in polymerized form, of from about 15 to about 60, preferably from about 35 to about 55, weight percent of the α,β-ethylenically unsaturated carboxylic acid; from about 1 to about 30, preferably from about 5 to about 20, weight percent of the unsaturated surfactant ester; and from about 15 to about 80, preferably from about 20 to about 60, weight percent of the nonionic chain extender monomer, said weight percentages being based on the total weight of the surfactant ester copolymer.

Although the molecular weight of the copolymers useful as copolymeric thickeners in this invention are not particularly critical to the practice of this invention, the preferred copolymers advantageously have a number average molecular weight of at least about 30,000, preferably from about 200,000 to about 5,000,000 when said molecular weight is determined by gel permeation chromatography.

Advantageously, the copolymeric thickener of the present invention is prepared in the form of a colloidal aqueous dispersion, i.e., a dispersion which consists of a continuous aqueous phase having distributed therethrough a discontinuous phase of finely divided copolymer particles of a colloidal size (about 1 mμ to about 1 μm), by subjecting an appropriate monomer mixture to conventional emulsion polymerization techniques.

The emulsion polymerization is advantageously conducted in an aqueous acidic liquid with said acidic liquid preferably having a pH such that the resulting copolymer is insoluble therein (e.g., a pH of less than about 4.5) and in the presence of an emulsifier and a free radical initiation means. Although other polymerization techniques can also be employed for preparing the copolymers of this invention (with subsequent conversion of the copolymer to the form of an aqueous colloidal dispersion), such other methods are not normally preferred herein.

Suitable free radical initiators include conventional chemical free radical initiators (UV light). Representative examples thereof include the peroxides such as hydrogen peroxide, benzoyl peroxide, acetyl peroxide, peracetic acid and lauroyl peroxide; persulfates such as ammonium persulfates, potassium persulfate and sodium persulfate; hydroperoxides such as cumene hydroperoxide and t-butyl hydroperoxide; azo compounds such as azobisisobutyronitrile, and redox initiators which are generally activated by a water-soluble reducing agent such as a ferrous compound or sodium bisulfite. In general, the initiator is advantageously employed in amounts which range from about 0.01 to about 5 weight percent based on the total weight of the monomers.

Typically, emulsifiers advantageously employed herein are conventional emulsifiers employed heretofore in the polymerization of emulsion polymerizable monomers. Generally, the emulsion polymerization is conducted in the presence of at least one anionic surfactant. Representative examples of anionic surfactants useful herein include the alkali metal alkylaryl sulfonates, e.g., sodium dodecylbenzenesulfonate and disodium dodecyldiphenyl ether disulfonate; the alkali metal alkyl sulfates, e.g., sodium lauryl sulfate; and the sulfonated alkyl esters, e.g., sodium dioctylsulfosuccinate. Optionally, a nonionic surfactant such as those nonionic surfactants described hereinbefore are employed in the polymerization.

To help control the molecular weight of the copolymer product resulting from the emulsion polymerization, a chain transfer agent is optionally employed in the practice of this invention. Representative chain transfer agents useful herein include carbon tetrachloride; bromoform; bromotrichloromethane; long chain alkyl mercaptans and thioesters such as n-dodecyl mercaptan, t-dodecyl mercaptan, octyl mercaptan, tetradecyl mercaptan, butyl thioglycolate, isooctyl thioglycolate and dodecyl thioglycolate. When employed, such chain transfer agents are generally advantageously employed in amounts from about 0.01 to about 10, preferably from about 0.01 to about 1, weight percent based on the total weight of the monomers employed.

Other materials well known in the art such as chelating agents, buffering agents, inorganic salts and pH adjusting agents can optionally be employed herein.

Generally, polymerization is advantageously conducted at temperatures from about 50° to about 110°C., preferably from about 60° to about 90°C. Typically, the amount of monomer employed is such that the polymeric solids in the resulting reaction product, i.e., aqueous dispersion of colloidal size copolymer particles, is from about 10 to about 65, preferably from about 20 to about 40, weight percent of the total weight of said dispersion. Advantageously, the discrete copolymer particles in the resulting polymerization product have a number average particle diameter of from about 500 Å to about 3000 Å, preferably from about 1000 Å to about 1750 Å, as measured by conventional light refraction techniques.

The amount of the copolymeric thickener most advantageously employed in preparing the thickened amphoteric surfactant composition will vary depending on the specific copolymer employed and the type and concentration of the amphoteric surfactant. Any amount which thickens the amphoteric surfactant composition without substantially reducing the clarity thereof is suitably employed herein. Typically, the copolymeric thickener is employed in amounts such that the resulting thickened amphoteric surfactant composition is normally liquid. Generally, for such purpose, the copolymeric thickener is employed at from about 0.1 to about 10, preferably from about 0.2 to about 5, more preferably from about 0.5 to about 2, weight percent based on the weight of the thickened amphoteric surfactant composition, i.e., aqueous liquid, amphoteric surfactant and the copolymeric thickener.

In some applications, however, the copolymeric thickener is more advantageously employed in amounts sufficient to form a gel-like material, i.e., a semi-solid having a jelly like consistency. In preparing such gel-like materials, the surfactant ester copolymer is the preferred copolymeric thickener and is generally employed at a concentration of at least about 1.5, more generally from about 2 to about 10, weight percent based on the total weight of the thickened amphoteric surfactant composition.

In general, within the above limits, the viscosity generally increases with increasing amounts of the copolymeric thickener. However, maximum viscosity is normally achieved, particularly with the surfactant ester copolymer, when the concentration of the copolymeric thickener in the thickened amphoteric surfactant composition ranges from about 10 to about 15 percent of the concentration of the amphoteric surfactant. Such amounts of the copolymeric thickener are thus most preferred.

In addition, the type and amount of copolymeric thickener is often advantageously selected such that the resulting thickened amphoteric surfactant composition exhibits pseudoplastic flow properties. Due to the ability of the surfactant ester copolymer to efficiently prepare such a pseudoplastic amphoteric surfactant composition, it is advantageously employed for such purpose.

The pH of the thickened, amphoteric surfactant compositions of this invention is suitably any pH at which the copolymer is soluble or sufficiently swollen to cause thickening without substantially reducing clarity. Advantageously, the composition has a pH of at least about 5.5, preferably at least about 6.5. More preferably, the composition is at a neutral or alkaline pH.

In preparing the thickened amphoteric surfactant compositions of this invention, the hereinbefore specified amounts of water, copolymeric thickener and amphoteric surfactant are mixed to form a thickened, amphoteric surfactant. Although the copolymeric thickener and amphoteric surfactant can be mixed in a variety of ways, in general, the amphoteric surfactant, advantageously in combination with any optionally employed ingredients, is advantageously added to an aqueous colloidal dispersion of the copolymeric thickener while said dispersion is agitated sufficiently to cause intimate and continuous contact between the surfactant and copolymer dispersion. Preferably, prior to the addition of the surfactant to the copolymer dispersion, the dispersion is diluted with an amount of water which provides the resulting thickened amphoteric surfactant composition with the desired amounts of the copolymeric thickener, amphoteric surfactant and water. The amphoteric surfactant is advantageously not diluted prior to its addition to the copolymer dispersion, i.e., it is employed in its commercially available form. Generally, the copolymeric thickener is sufficiently solubilized or swollen in the resulting mixture to cause thickening thereof. If necessary, however, sufficient amounts of an alkaline material, i.e., NaOH, can be added to the resulting combination to solubilize or swell the polymer to obtain the desired viscosity increases.

Alternatively, although less preferred, sufficient amounts of an alkaline material are added to the copolymer dispersion to solubilize or swell the polymer. The amphoteric surfactant is then combined with the resulting copolymer solution to form a thickened, amphoteric surfactant composition.

Optionally, the thickened amphoteric surfactant composition can contain other ingredients including small amounts of an anionic surfactant such as the alkyl substituted aromatic sulfonates (e.g., alkyl benzenesulfonate) and the sulfates of aliphatic alcohols or alcohol ethers (e.g., lauryl ether sulfonate or alkali metal salt thereof); cationic surfactants such as distearyldimethyl ammonium chloride, dilauryl dimethyl ammonium chloride and N-cetyl pyridinium bromide; and nonionic surfactants such as the condensation product of an alkylene oxide (e.g., ethylene oxide) with a long chain (i.e., 6 to about 20 carbon atoms) fatty alcohol, long chain fatty acid, alkylated phenol or long chain alkyl primary amine (e.g., polyoxyethylene sorbitan monolaurate wherein x is from about 20 to about 80).

The following examples are set forth to illustrate the advantages of the present invention and should not be construed to limit its scope. In the examples, all parts and percentages are by weight unless otherwise indicated.

EXAMPLE 1

To a stainless steel reactor equipped with a heating and cooling means, stirrer and addition funnel and containing 474 parts of nonylphenoxypoly(ethyleneoxy)9ethanol, 0.31 part of hydroquinone and 0.16 part of 2,6-di-t-butyl-p-cresol is added, with agitation, 8.6 parts of an aqueous solution of 90 percent sulfuric acid, followed by the addition of 526 parts of methacrylic acid stabilized with monomethyl ether of hydroquinone. While bubbling a slow stream of air through the reaction mixture, the reactor is heated for 2 hours at 105°C. At the end of this period, the reactor is cooled to room temperature, i.e., room temperature being from about 18° to about 25°C., and the liquid reaction product recovered. This reaction product is found to contain 47.2 percent of a vinyl surfactant ester, which corresponds to about 90 percent conversion, 4.8 percent unreacted nonylphenoxypoly(ethyleneoxy)9-ethanol, 46.8 percent excess methacrylic acid and 1.2 percent water, sulfuric acid and stabilizers.

To a stainless steel reactor similar to the reactor employed in preparing the surfactant ester is added 374 parts deionized water, 0.008 part of sodium diethylenetriamine pentaacetic acid (40 percent solids) sold as Versenex ® 80 by The Dow Chemical Company and 2 parts of a nonylphenoxypoly(ethyleneoxy)phosphate ester in free acid form sold as Gafac ® RE-610 by GAF Corporation. A feed stream of 48 parts methacrylic acid, 42 parts ethyl acrylate, 10 parts of the vinyl surfactant ester prepared by the aforementioned method, and 6 parts of a nonionic surfactant sold as Igepal ® CO-530 by GAF Corporation is continuously added to the reactor over a 4 hour period. Concurrent therewith, an aqueous feed mixture of 69.8 parts deionized water, 0.0025 part Versenex ® 80, 0.4 part sodium hydroxide, 2 parts of sodium dodecyldiphenyl ether disulfonate sold as Dowfax ® 2A1 by The Dow Chemical Company, 1 part Gafac ® RE-610 and 0.5 part sodium persulfate is continuously added to the reactor over a 4 hour period. During these additions, the reactor is maintained at a temperature of about 70°C. At the end of this addition, the temperature of the reactor is raised to about 80°C. The reactor is maintained at this temperature for 1.5 hours. The reaction mixture is then cooled and filtered through 100 and 200 mesh (Tyler standard screen size).

The resulting aqueous dispersion of colloidal size copolymer particles contains 20.1 percent solids at a pH of about 3.5 and has a viscosity of 400 cps (Brookfield Viscometer, Model LVT, No. 2 Spindle, 12 rpm, 25°C.) as a 1 percent aqueous solution, in ammonium salt form (pH=9).

To a 3.8 part portion of the resulting copolymer dispersion is added 48.2 parts of deionized water. To form a thickened, amphoteric surfactant composition, 100 parts of an aqueous solution of 38 percent of an amphoteric surfactant of a dicarboxylated imidazoline derivative of a coconut fatty acid sold as Miranol ® C2M by Miranol Chemical Company, Inc. is added to the resulting diluted copolymer dispersion. The resulting thickened amphoteric surfactant composition (Sample No. 1) consists of amphoteric surfactant and about 0.5 part of the copolymeric thickener.

In a similar manner, several thickened amphoteric surfactant compositions (i.e., Sample Nos. 1–10) are prepared using the various amphoteric surfactants identified in Table I and containing the various amounts of the surfactant ester copolymer as recorded in Table I.

Each of the thickened amphoteric surfactant compositions is tested for clarity and viscosity. All the samples exhibited a light transmittance of at least 80 percent when measured by a Beckman UV spectrometer, Model DB-G. The results of the viscosity testing are recorded in Table I.

As a control, amphoteric surfactant compositions identical to Sample Nos. 1–10 except that they do not contain the copolymeric thickener are prepared. The viscosity of each of these unthickened surfactant solutions is measured. Each of the unthickened surfactant solutions has a viscosity of less than about 25 cps.

For comparison, 0.5 part of a hydroxypropyl methyl cellulose sold as Methocel ® E4-M by The Dow Chemical Company having a methoxyl degree of substitution of from about 1.8 to about 2.0 and a hydroxypropyl molar substitution of from about 0.2 to about 0.31 dissolved in 25 parts water is added to 75 parts of the aforedescribed amphoteric surfactant composition. The resulting mixture is found to be an unthickened two-phase system.

TABLE I

| Sample No. | Surfactant Type (1) | Wt % (2) | Copolymer Thickener % (3) | Viscosity, cps (4) |
|---|---|---|---|---|
| 1 | C2M | 25.0 | 0.5 | 150 |
| 2 | C2M | 25.0 | 1.8 | 8000 |
| 3 | HM | 9.5 | 0.5 | 3900 |
| 4 | 2MCT | 11.0 | 0.5 | 250 |
| 5 | 2MCT | 25.0 | 2.0 | 525 |
| 6 | 2MCAS | 9.5 | 0.5 | 34250 |
| 7 | 2MCAS | 25.0 | 0.5 | 2700 |
| 8 | L2MSF | 25.0 | 2.0 | 1650 |
| 9 | M2MSF | 25.0 | 2.0 | 475 |
| 10 | S2MSF | 25.0 | 2.0 | 225 |

(1) The type of surfactant is given in abbreviated form wherein:
C2M = a dicarboxylated imidazoline derivative of coconut fatty acid;
HM = a monocarboxylated imidazoline derivative of lauric acid;
2MCT = the polyoxyethylene (3) tridecyl sulfate salt of a dicarboxylated imidazoline derivative of coconut fatty acid;
2MCAS = an equimolar mixture of lauryl sulfate and the polyoxyethylene (3) dodecyl sulfate salts of a dicarboxylated imidazoline derivative of coconut fatty acid;
L2MSF = an essentially salt free dicarboxylated imidazoline derivative of tall oil fatty acid;
M2MSF = a dicarboxylic myristic derivative, sodium salt; and
S2MSF = an essentially salt free dicarboxylated imidazoline derivative of capric acid.
All of said amphoteric surfactants are available from Miranol Chemical Co., Inc.
(2) The weight percent of the surfactant (dry weight basis) in the thickened surfactant solution based on the weight of the amphoteric surfactant, copolymer and water.
(3) The weight percent of the copolymer in the thickened amphoteric surfactant composition based on the weight of the amphoteric surfactant, copolymer and water.
(4) The viscosity of the thickened amphoteric surfactant composition measured using a Brookfield viscometer, Model LVT, Spindle No. 2, 12 rpm at 20° C., the speed being increased to 20 rpm with solutions having viscosities greater than about 2500cps.

As evidenced by the data recorded in Table I, a wide variety of amphoteric surfactant compositions are effectively thickened by the method of this invention. The viscosity increase exhibited by each of the thickened amphoteric surfactant compositions is shown to be dependent on the type and amount of the amphoteric surfactant and the concentration of the polymeric thickener.

EXAMPLE 2

Separate portions of a commercially available baby shampoo sold by Johnson and Johnson as "No more Tears" and containing water, a lauryl sulfate derivative of a long chain N,N-hydroxyethyl amido amine classified as Amphoteric-19 in the CTFA Cosmetic Ingredient Dictionary, polyoxyethylene (2) sorbitan monolaurate (chemical description of the polyethylene glycol diester of stearic acid), sorbitan laurate, boric acid, fragrance and benzyl alcohol are added to colloidal aqueous dispersions of the various copolymeric thickeners specified in Table II, to form several thickened amphoteric surfactant compositions (Sample Nos. 1–4) containing the various amounts of the copolymeric thickener as specified in Table II. The thickened amphoteric surfactant compositions were tested for clarity and viscosity. None of the compositions exhibited a substantial reduction in clarity. The results of the viscosity testing are recorded in Table II. As a control, the viscosity of the baby shampoo containing no copolymeric thickener is measured and recorded in Table II.

TABLE II

| Sample No. | Copolymer Thickener (1) | Thickener, wt % (2) | Viscosity, cps (3) |
|---|---|---|---|
| C* | — | — | 465 |
| 1 | E9N10 | 0.5 | 1200 |
| 2 | E9N10 | 2.0 | 32000 |
| 3 | EB5E19 | 0.5 | 925 |
| 4 | EI9N10 | 0.5 | 675 |

*Not an example of this invention
(1) The copolymeric thickener is given in abbreviated form wherein:
E9N10 = a copolymer derived from 42 percent ethyl acrylate, 48 percent methacrylic acid and 10 percent nonylphenoxypoly(ethyleneoxy)$_9$ methacrylate;
EB5E19 = a copolymer derived from 42 percent ethyl acrylate, 48 percent methacrylic acid and 10 percent poly(butyleneoxy)$_5$poly(ethyleneoxy)$_{19}$ ethyl methacrylate; and
EI9N10 = a copolymer of 42 percent ethyl acrylate, 42 percent methacrylic acid, 6 percent itaconic acid and 10 percent nonylphenoxypoly(ethyleneoxy)$_9$ methacrylate. Such copolymers are prepared in a manner similar to that of Example 1.
(2) The weight percent of the copolymer in the thickened amphoteric surfactant composition.
(3) Same as (4) in Table I.

In addition to the above testing, to measure the effect of heat aging on the thickened amphoteric surfactant compositions a portion of Sample Nos. C, 1 and 2 are placed in a circulating hot air oven maintained at a temperature of 55° C. After being stored in the hot air oven for 144 hours, the portions are removed, cooled to room temperature and the viscosity of each portion measured. The viscosity of Sample C is found to be about 420 cps, representing a viscosity retention of about 91 percent. The viscosity of Sample 1 remained 1200 cps representing a viscosity retention of 100 percent, and the viscosity of Sample 2 is measured as 19,700 cps.

As evidenced by the data recorded in Table II, amphoteric surfactant compositions are effectively thickened using various surfactant ester copolymeric thickeners. After heat aging, the viscosity of the thickened surfactant compositions (i.e., Sample Nos. 1 and 2) continue to exhibit higher viscosities than the unthickened surfactant solution (Sample No. C).

EXAMPLE 3

An aqueous solution is prepared having the following ingredients:

| Ingredient (1) | Solid Parts | Liquid Parts |
|---|---|---|
| HM | 4.0 | 9.5 |
| LCAB | 4.0 | 9.1 |
| POE44SML | 6.5 | 9.1 |
| POE80SML | 3.5 | 4.9 |
| STEOL4N | 6.0 | 21.4 |
| HCL (15%) | 0.2 | 1.3 |
| DI Water | — | 44.7 |

(1) The ingredients are given in abbreviated form wherein:
HM = the monocarboxylated imidazoline derivative of lauric acid (42 percent aqueous solution) sold as Miranol ® HM by Miranol Chemical Company;
LCAB = N—hydroxyethylaminoethyl cocoamideacrylic acid betaine (44 percent aqueous solution) sold as Lonzaine 12C by Lonza, Inc.;
POE44SML = poly(oxyethylene)44 sorbitan monolaurate (72 percent aqueous solution);
POE80SML = poly(oxyethylene)80 sorbitan monolaurate (72 percent aqueous solution);
STEOL4N = lauryl ether sulfate (28 percent aqueous solution);
HCL (15%) = an aqueous solution of 15 percent hydrochloric acid; and
DI Water = deionized water.

Several samples (Sample Nos. 1–8) are prepared by adding separate portions of the resulting: aqueous solution to several colloidal aqueous dispersions of the various copolymers identified in Table III. The resulting samples contain the amount of the copolymer specified in Table III. A portion of the amphoteric surfactant composition having no copolymer added thereto (Sample No. C) is employed as a control. Each of the samples is tested for clarity and viscosity. The results of this testing are recorded in Table III.

TABLE III

| Sample No. | Copolymer Type (1) | Wt % (2) | Viscosity cps (3) | Clarity % Trans (4) |
|---|---|---|---|---|
| C* | — | — | 250 | 99 |
| 1* | EAM-1 | 1.0 | 250 | 2 |
| 2* | EAMMEO | 1.5 | 1950 | 45 |
| 3 | EAM-2 | 1.4 | 5750 | 52 |
| 4 | EAM-3 | 1.5 | 2500 | 94 |
| 5 | MMAA | 1.5 | 17250 | 87 |
| 6 | EAM-4 | 1.5 | 8500 | 88 |
| 7 | E9N-10 | 1.0 | 4450 | 95 |
| 8 | E9N-10 | 1.5 | — | — |

*Not an example of this invention
(1) The copolymers are listed in abbreviated form wherein:
EAM-1 consists of a copolymer of ethyl acrylate and methacrylic acid sold as ASE-95 by Rohm & Haas Company;
EAMMEO consists of a copolymer of methyl acrylate, methyl methacrylate, methacrylic acid and having an adduct of poly(ethylene oxide) sold as NL Rheolate 1 by NL Industrial Chemicals, NL Industries, Inc.;
EAM-2 consists of a copolymer of ethyl acrylate and methacrylic acid sold as Alcogum L11 by Alco Chemicals Corp.;
EAM-3 consists of a copolymer of ethylacrylate and methacrylic acid sold as RM 4 by Rohm & Haas Company;
MMAA consists of a copolymer of the ethyl ester of methacrylic acid and acrylic acid sold as Viscalex EP-30 by European Allied Colloids;
EAM-4 consists of a copolymer of ethyl acrylate and methacrylic acid sold as Alcogum L15 by Alco Chemicals Corp.; and
E9N-10 is a copolymer derived from 42 percent ethyl acrylate; 48 percent methacrylic acid and 10 percent nonylphenoxypoly(ethyleneoxy)-methacrylate.
(2) Same as (3) in Table II.
(3) Same as (4) in Table I.
(4) Clarity is reported as the percent of visible light transmitted through the composition as measured using a Beckman DB-G UV spectrophotometer. The compositions appear clear at or above a light transmittance of about 50 percent. Below 50 percent light transmittance the compositions are noticeably cloudy.

In addition to the viscosity and clarity testing, separate portions of Sample No. C and Sample No. 7 are placed in a hot air oven maintained at a temperature of 60°C. for a period of 17 hours. The samples are then removed from the oven and allowed to cool to room temperature. The viscosity of the control (Sample No. C) is found to be 200 cps, indicating a viscosity retention of about 80 percent. The viscosity of Sample No. 7, an example of a thickened amphoteric surfactant composition of this invention is found to be about 4000 cps, indicating that about 90 percent of the original viscosity is retained.

As evidenced by the data in Table III, combining the amphoteric surfactant composition with a suitable copolymeric thickener thickens the amphoteric surfactant composition without substantially reducing the clarity thereof. Moreover, the data indicates the amphoteric surfactant composition thickened using the preferred surfactant ester copolymer possesses the most desirable balance of viscosity and clarity.

The substantially reduced clarity exhibited by Sample Nos. 1 and 2 is believed to be due to incomplete solubilization of the copolymer in the aqueous solution containing the amphoteric surfactant.

EXAMPLE 4

A thickened amphoteric surfactant composition is prepared by adding 100 parts of an aqueous solution of 41 percent N-hydroxyethylaminoethyl cocoamide-acrylic acid betaine to 37.8 parts of a copolymer dispersion containing 2.8 parts of a copolymer similar in all respects to the copolymer of Example 1. The resulting thickened amphoteric surfactant composition consists of about 30 percent, by weight, of the amphoteric surfactant, 2 percent, by weight, of the copolymer and 68 percent, by weight, of water and is designated Sample No. 1.

As a control, an aqueous solution containing 41 percent N-hydroxyethylaminoethyl cocoamide-acrylic acid betaine is prepared (Sample No. C).

Each sample is tested for viscosity, clarity, wetting time, surface tension and foam height. The thickened amphoteric surfactant composition is found to transmit more than 90 percent of the light transmitted by the control. The results of the remainder of the testing are recorded in Table IV.

TABLE IV

| Sample No. | Viscosity, cps (1) | Wetting Time, Sec (2) | Surface Tension, Dynes/cm (3) | Foam Height, mm (4) | | |
|---|---|---|---|---|---|---|
| | | | | 0 min | 2 min | 5 min |
| C* | 700 | 94.0 | 25.8 | 48 | 43 | 40 |
| 1 | 13,750 | 95.6 | 25.7 | 62 | 53 | 50 |

*Not an example of this invention
(1) Same as (4) in Table I.
(2) Wetting time of the surfactant solutions as determined using the Draves-Clarkson test method.
(3) Surface tension of the surfactant solutions as determined using ASTM method designated D-1331-56.
(4) Foam height of the surfactant solutions as determined using ASTM method designated D-1173-53.

As evidenced by the data in Table IV, the amphoteric surfactant solutions thickened with a surfactant ester copolymer exhibit an increased viscosity without a reduction in foam height, surface tension or wetting time. Thus, such thickened amphoteric surfactant compositions are suitable as cleansing or shampoo compositions.

What is claimed is:

1. A thickened, amphoteric surfactant composition comprising an aqueous solution of a water-soluble amphoteric surfactant thickened with a pH responsive, synthetic addition copolymer which is insoluble in an aqueous liquid at a pH of less than about 2, said composition being at a pH and containing an amount of the pH responsive copolymer sufficient to increase the viscosity of the amphoteric surfactant composition without substantially reducing the clarity thereof.

2. The thickened composition of claim 1 wherein the thickened composition exhibits a light transmittance of at least about 50 percent and a viscosity which is at least about 500 percent higher than the viscosity of an identical amphoteric surfactant solution containing no thickener therein.

3. The thickened composition of claim 2 wherein the thickened composition transmits at least 80 percent of the light transmitted by the unthickened, amphoteric surfactant solution and exhibits a viscosity of at least 1000 percent higher than the viscosity of an identical amphoteric surfactant composition containing no thickener therein.

4. The thickened composition of claim 1 wherein the amphoteric surfactant is an alkyl-substituted imidazoline; an alkyl aminobetaine; a N-alkyl β-aminopropionic acid, an alkyl-3-aminopropionic acid or a salt thereof and fatty acid amide sulfonate.

5. The thickened composition of claim 4 wherein the amphoteric surfactant is an alkyl-substituted imidazoline or an alkyl aminobetaine and the thickened composition consists of from about 1 to about 35 weight percent of amphoteric surfactant.

6. The thickened composition of claim 1 wherein the copolymeric thickener is a copolymer of (a) an α,β-ethylenically unsaturated carboxylic acid and (b) an alkyl ester of an α,β-ethylenically unsaturated carboxylic acid.

7. The thickened composition of claim 6 wherein the copolymeric thickener is a copolymer of from about 8 to about 70 weight percent methacrylic acid and from about 92 to about 30 weight percent of ethylacrylate or methyl methacrylate, said weight percents being based on the total weight of methacrylic acid, ethylacrylate or methyl methacrylate.

8. The thickened composition of claim 7 wherein the copolymeric thickener is a copolymer of (a) a vinyl ester of a nonpolymerizable carboxylic acid, (b) a nitrile, a hydroxyalkyl ester or an alkyl ester of an α,β-ethylenically unsaturated carboxylic acid and (c) an α,β-ethylenically unsaturated carboxylic acid.

9. The thickened composition of claim 8 wherein the vinyl ester is vinyl acetate, vinyl propionate or vinyl benzoate; the nitrile is acrylonitrile, the hydroxyalkyl ester is 2-hydroxyethyl acrylate and the alkyl ester is ethylacrylate; and the unsaturated carboxylic acid is methacrylic acid.

10. The thickened composition of claim 1 wherein the copolymeric thickener is a surfactant ester copolymer of (a) an α,β-ethylenically unsaturated carboxylic acid; (b) a nonionic surfactant ester of an α,β-ethylenically unsaturated carboxylic acid and (c) a polymeric chain extender of an α,β-ethylenically unsaturated monomer copolymerizable with the unsaturated carboxylic acid and unsaturated surfactant ester.

11. The thickened composition of claim 10 wherein the α,β-ethylenically unsaturated carboxylic acid is of the formula:

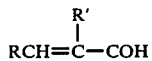

wherein R is —H, —COOX or —CH$_3$; R' is —H, an alkyl group or —CH$_2$COOX and X is —H or an alkyl group; the unsaturated surfactant ester is represented by the formula:

$$H_2C=\underset{\underset{R}{|}}{C}-\underset{\underset{}{\overset{\overset{O}{\|}}{}}}{C}(OC_2H_4)_n(O\underset{\underset{R'}{|}}{C}HCH_2)_mOR''$$

wherein R is H or CH₃; R'' is an alkyl group or an alkylphenyl group; each R' is individually —H, —CH₃ or —C₂H₅; n is an integer from about 0 to 100 and m is an integer from about 0 to 100 and the sum of m+n is at least 1; and the polymeric chain extender monomer is represented by the formula:

$$CH_2=CYZ$$

wherein Y is —H or —CH₃ or a halogen and Z is —COOR where R is an alkyl group or hydroxyalkyl group, —C₆H₄R' where R' is —H, an alkyl group or a halogen; —Cl; —Br; —CN;

$$-\overset{\overset{O}{\|}}{O}CR''$$

where R'' is an alkyl group; or —CH=CH₂.

12. The thickened composition of claim 11 wherein the surfactant ester copolymer comprises (a) from about 15 to about 60 weight percent of the α,β-ethylenically unsaturated carboxylic acid of the formula:

$$RCH=\underset{\underset{R'}{|}}{C}-COOH$$

wherein R is —H and R' is —H, —CH₂COOX or an alkyl group having from about 1 to about 4 carbon atoms; R is —COOX and R' is —H or —CH₂COOX or R is —CH₃ and R' is —H; and X is —H or an alkyl group having from about 1 to about 4 carbon atoms; (b) from about 1 to about 30 weight percent of the unsaturated surfactant ester of the formula:

$$H_2C=\underset{\underset{R}{|}}{C}-\underset{\underset{}{\overset{\overset{O}{\|}}{}}}{C}(OC_2H_4)_n(O\underset{\underset{R'}{|}}{C}HCH_2)_mOR''$$

and R is —H or —CH₃; R' is —H or an alkyl group of 1 or 2 carbon atoms; R'' is an alkyl group of from 1 to about 20 carbon atoms or an alkylphenyl group of from about 8 to about 16 carbon atoms; and n and m are integers from about 0 to 100 with n being 1 or more and greater than m and the sum of n+m is from 1 to about 100; and (c) from about 15 to about 80 weight percent of the polymeric chain extender monomer of the formula:

$$CH_2=CYZ$$

and Y is —H, Z is —COOX', —C₆H₄Y', —CN, —Cl, $$-\overset{\overset{O}{\|}}{O}CZ'$$

—CH=CH₂; Y is —CH₃ and Z is —COOX; —C₆H₄Y', —CN, or —CH=CH₂; or Y and Z are —Cl; where X' is an alkyl group of having from about 1 to about 8 carbon atoms or a hydroxyalkyl group having from about 2 to about 8 carbon atoms; Y' is —H, —Cl, —Br or an alkyl group of about 1 to about 4 carbon atoms; and Z' is an alkyl group of from about 1 to about 8 carbon atoms.

13. The thickened composition of claim 12 wherein the α,β-ethylenically unsaturated carboxylic acid is methacrylic acid, acrylic acid or a mixture of acrylic or methacrylic acid with itaconic or fumaric acid and the polymeric chain extender monomer is a monovinyl ester or mixture thereof with styrene, hydroxyethyl acrylate, acrylonitrile, vinyl chloride or vinyl acetate.

14. The thickened composition of claim 13 wherein the unsaturated carboxylic acid is methacrylic acid or a mixture thereof with itaconic acid which, in polymerized form, constitutes from about 35 to about 55 weight percent of the surfactant ester copolymer; and the polymeric chain extender monomer is ethylacrylate which, in polymerized form, constitutes from about 20 to about 60 weight percent of the surfactant ester copolymer.

15. The thickened composition of claim 11 wherein the unsaturated surfactant ester is an alkylphenoxypoly(ethyleneoxy)ethylacrylate of the formula:

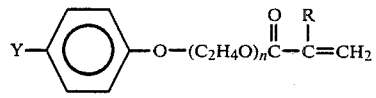

wherein R is H or CH₃; Y is an alkyl group having about 8 to about 16 carbon atoms and n is from about 2 to about 100.

16. The thickened composition of claim 11 wherein the unsaturated surfactant ester is an alkoxypoly(ethyleneoxy)ethylacrylate of the formula:

$$R''O-(C_2H_4O)_n-\overset{\overset{O}{\|}}{C}-\underset{\underset{R}{|}}{C}=CH_2$$

where R is —H or —CH₃, R'' is an alkyl group having from about 8 to about 20 carbon atoms and n is from about 6 to about 50.

17. The thickened composition of claim 11 wherein the unsaturated surfactant ester alkoxypoly(alkyleneoxy)ethylacrylate of the formula:

$$R''O(CH_2\underset{\underset{R}{|}}{C}HO)_n(C_2H_4O)_mC_2H_4O-\overset{\overset{O}{\|}}{C}-\underset{\underset{R}{|}}{C}=CH_2$$

wherein R is —H or —CH₃, R' is —CH₃ or —C₂H₅, R'' is an alkyl group having from about 1 to about 20 carbon atoms, n is from about 6 to about 50 and m is from about 1 to about 14.

18. A method for preparing a thickened amphoteric surfactant composition, said method comprising the step of thickening an aqueous solution of the water-soluble amphoteric surfactant with an amount of a pH responsive, synthetic addition copolymeric thickener sufficient to increase the viscosity of the resulting aqueous amphoteric surfactant composition without substantially reducing the clarity thereof.

* * * * *